United States Patent [19]

Behar et al.

[11] Patent Number: 4,554,317

[45] Date of Patent: Nov. 19, 1985

[54] SYNTHETIC WOUND COVERING

[76] Inventors: David Behar, 4 Habanai St., Jerusalem 96264, Israel; Arie L. Rajbenbach, 11 Herzog St., Givatayim 53600, Israel; Marta Juszynski, 43/9 Epstein St., Rehovot, Israel; Nahum Ben-Hur, 8 Bialik St., Jerusalem 96221, Israel

[21] Appl. No.: 539,586

[22] Filed: Oct. 6, 1983

Related U.S. Application Data

[63] Continuation-in-part of Ser. No. 481,899, Apr. 4, 1983, abandoned.

[30] Foreign Application Priority Data

Apr. 6, 1982 [IL] Israel ......................................... 65438

[51] Int. Cl.$^4$ ........................ C08G 18/67; A61L 15/01
[52] U.S. Cl. ....................................... 525/28; 128/156; 204/159.19; 514/953; 604/304
[58] Field of Search ................... 128/156; 204/159.19; 525/28, 454; 424/26, 28, 78

[56] References Cited

U.S. PATENT DOCUMENTS

| | | | |
|---|---|---|---|
| 3,262,450 | 7/1966 | Elias | 424/28 |
| 3,454,011 | 7/1969 | Wagner | 128/156 |
| 3,645,835 | 2/1972 | Hodgson | 161/146 |
| 3,669,934 | 6/1972 | Epstein et al. | 264/235.6 |
| 3,800,792 | 4/1974 | McKnight et al. | 128/156 |

OTHER PUBLICATIONS

Ratner, B. D. et al., "Synthetic Hydrogels for Biomedical Applications", Hydrogels for Medical and Related Applications, ACS Publication, Joseph D. Andrade, Editor, pp. 1 to 36 (1976).
Merrill, E. W. et al., "A Critical Study of Segmented Polyurethanes", Biomaterials: Interfacial Phenomena and Applications, ACS Publication, Cooper, S. L., et al., Editors, pp. 95 to 107 (1982).
Wilkes, G. L., "Necessary Considerations for Selecting a Polymeric Material for Implantation with Emphasis on Polyurethanes", Polymers in Medicine and Surgery, Polymer science and Technology, vol. 8, Kronenthal, R. L. et al., Editors, pp. 45 to 75 (1975).
Science, 158, pp. 1481-1482, 1967.
Ossefort et al., "Hydrolytic Stability of Urethan Elastomers", Rubber Chem. & Tech., Sep. 1966, vol. 39, No. 4, pp. 1309-1327.
Magnus G. et al., "Stability of Urethan Elastomers . . . ", Rubber Chem. & Tech., Sep. 1966, vol. 39, No. 4, pp. 1328-1327.
Gott, V. L. et al., "Antithrombogenic Surfaces . . . ", Federation Proceedings, vol. 30, No. 5, pp. 1679-1685, Sep.-Oct. 1971.
Bruck, Stephen, "Consideration of Species Related Hematological differences on the Evaluation of Biomaterials", Biomat., Med. Dev., Art. Organs, 5(1), 97-113, 1977.
Bruck, Stephen, "Some Current Problems and New Dimensions of Polymeric Biomaterials for Blood-Contacting Applications", Biomat., Med. Dev. Art. Organs, 6(1), 57-76, 1978.
Dror, M. et al., "Interpenetrating Polymer Networks for Biological Applications", Biomat., Med. Dev., Art. Organs, 7(1), 31-39, 1979.
Hoffman, A. S., et al., "Radiation Grafted Hydrogels on Polyurethane Surfaces—A New Biomaterial", Am. Chem. Soc., Polymer Preprints, vol. 13, No. 2, Aug. 1972, pp. 723-728.
Lee, H. B. et al., "Radiation Grafting of Synthetic Hydrogels to Inert Polymer Surfaces I. Hydroxyethyl Methacrylate", Am. Chem. Soc., Polymer Preprints, vol. 13, No. 2, Aug. 1972, pp. 729-735.
B. Jansen et al., (1979) J. Polymer Sci.: Polymer Symp. 66:465-473, "Radiation-Induced Modification . . . Hydroxyethyl Mathacrylate".
B. Ratner, et al., (1978) J. Appl. Polymer Sci. 22:643-664, "Radiation-Grafted Hydrogels for Biomaterial . . . ESCA Technique".
B. D. Halpern et al., (1974) N.T.I.S., PB-230 310, pp. 1-32, "Polymer Studies Related to Prosthetic . . . Blood Interface".
A. Hoffman et al., (1979) Radiat. Phys. Chem., 14:831-840, "The Radiation Grafting of Acrylamide . . . Of Cupric Ion".
H. B. Williams, (1983) IPRS, Meeting of the Int. Conf. Plas., "Transactions of the VIII Int. Congress of Plastic and Reconstructive Surgery", Montreal, Canada, Jun. 26-Jul. 1, 1983.
Jansen et al. (1981) Radiat. Phys. Chem. 18:1195-1202.

*Primary Examiner*—Veronica P. Hoke
*Attorney, Agent, or Firm*—Townsend & Townsend

[57] ABSTRACT

A synthetic hydrophilic membrane is prepared by graft polymerization of hydrophilic monomers with a polyurethane substrate. The resulting material has a water permeability in the range from about 1,000 to 8,000 g/m$^2$/24hr. The material is particularly useful as a wound covering material where such water permeability corresponds to the elevated water loss from open wounds and allows the wound to heal without desiccation or water accumulation under the covering.

21 Claims, No Drawings

SYNTHETIC WOUND COVERING

This application is a continuation-in-part of application Ser. No. 481,899 filed on Apr. 4, 1983, now abandoned, which application claimed priority from Israeli application Ser. No. 65438, filed Apr. 6, 1982.

BACKGROUND OF THE INVENTION

1. Field of the Invention

Wounds resulting from burns, severe abrasions, skin ulcers, skin transplants, and the like often affect relatively large areas of skin and are particularly vulnerable to infection. To protect such wounds, particular dressings or coverings have been developed which are often referred to as "synthetic skins" or "artificial skins." Such artificial skins should have a number of properties in order to effectively protect the wound while healing or prior to subsequent treatment such as homographt. First, they must have an optimal water permeability which avoids fluid accumulation under the covering while simultaneously preventing desiccation of the wound. This is a particular problem in view of the high rate of water loss in wounds where the epidermal layer has been partially or completely lost, typically in the range from about 3400 to 5200 g/m$^2$/24 hr. See, Lamke (1977) Burns 3:159. This compares to an average water loss through the epidermal layer on the order of 240 g/m$^2$/24 hrs.

The material used as an artificial skin should also act as a barrier to prevent microbial invasion, be flexible so that it will conform to the wound as the body is in motion, inhibit scar formation and be capable of adhering to the wound while allowing intentional removal without damage to the underlying tissue. The material must also be biocompatible, i.e., be non-toxic, non-antigenic and non-irritating.

Heretofore, various polymeric membranes have been developed for use as wound coverings. One such wound covering which is commercially available is Op-Site ®, manufactured by T. J. Smith and Nephew Ltd., Kingston-Upon-Hull, United Kingdom. Op-Site ® is a thin polyurethane film having a pressure-sensitive layer on one surface. Although useful, the Op-Site ® dressing suffers from certain disadvantages. It displays limited water permeability, typically on the order of 500 g/m$^2$/24 hr. Such low permeability often leads to fluid accumulation under the dressing. Also, the application of an adhesive on the wounded area can sometimes irritate or inflame the wound.

Therefore, it would be desirable to provide a synthetic wound covering having the desirable characteristics set forth above.

2. Description of the Prior Art

U.S. Pat. No. 3,645,835 to Hodgson describes polymeric wound coverings comprising a layer of a synthetic polymer, e.g., polyurethane, having a pressure-sensitive adhesive on one surface. This patent appears to cover the Op-Site ® material described above. Other commercially available polymeric bandaging materials include Epigard, a laminate formed from a polyurethane foam and a polypropylene film which is available from Parke Davis Co., Detroit, Mich. and Lyofoam, a polyurethane foam heated on one surface to form a film. U.S. Pat. No. 3,800,792 describes a polyurethane collagen composite used as a bandaging material. The grafting of hydrophilic monomers onto hydrophobic polymers is known. See, e.g., Chapiro, "Radiation Chemistry of Polymeric Systems," Interscience, Academic Press, London 1962. Radiation-induced grafting of acrylic monomers onto the surface of a polyurethane film is described in Ratner et al. (1978) J. Appl. Polym. Sci. 22:643–664, and Hoffman and Ratner (1979) Rad. Phys. Chem. 14:831–840. Jansen and Ellinghorst (1979) J. Polym. Symp. 66:465–473 disclose a pre-swelling technique to form an interpenetrating network of hydroxyethyl methacrylate and a polyether polyurethane. Cerium (Ce$^{+4}$) salt was used as an initiator for grafting of polyacrylamide onto the surface of a polyurethane film. See, Halpern et al. Annual Report PH-43-66-1124-6, PB-230, National Institutes of Health (1974). A paper describing clinical results obtained using the wound covering of the present invention was presented at the VII International Congress of Plastic and Reconstructive Surgery, Montreal, Canada, June 26–July 1, 1983, Transactions pp. 26–27. A similar paper was presented in San Francisco at the VI International Congress on Burns, Aug. 29–Sept. 1, 1982.

SUMMARY OF THE INVENTION

According to the present invention, a synthetic hydrophilic membrane is produced by graft polymerization of hydrophilic monomers onto a polyester polyurethane substrate. The product is a homogenous graft copolymer where the (polymerized) monomers substantially penetrate and are substantially uniformly dispersed throughout the substrate to produce a novel hydrophilic membrane which finds particular use as a wound covering or dressing. By selecting particular hydrophilic monomers and controlling the reaction conditions under which the monomers are introduced, the water permeability of the wound covering may be adjusted within a desired range from about 1,000 to 8,000 g/m$^2$/24 hr. Although water permeable, the membrane acts as a barrier and prevents microbial invasion. Such wound coverings are relatively inelastic and non-adhesive when dry, facilitating storage. The coverings, however, are highly elastic when wet and, as a result of their hydrophilic surface, are capable of adhering to a wound without the need for an adhesive or external means for securing the covering. Moisture from the wound itself is usually sufficient to wet the covering, although the covering may be wetted prior to application if desired. Additionally, the covering material of the present invention is transparent, allowing observation of the wound without the need to remove the covering.

DESCRIPTION OF THE SPECIFIC EMBODIMENTS

The present invention provides a novel hydrophilic membrane material which is particularly suitable as a wound covering. The material displays enhanced water permeability which allows an optimum water flux from the wound. The material comprises a polyurethane substrate or membrane which is graft polymerized with a hydrophilic monomer to form a novel hydrophilic, water permeable composition where the (polymerized) monomer is substantially uniformly dispersed throughout the bulk of the substrate. The resulting membranes are highly elastic, having a modulus of elasticity below about 600 PSI when wet. The compositions of the present invention are prepared by free radical graft polymerization in the presence of a homopolymerization inhibitor.

Although the hydrophilic membrane of the present invention will find its primary use as a wound covering material, it may also be employed in a variety of medical, scientific and industrial applications which require semipermeable membranes. For example, the material may be used as a dialysis membrane, and the like.

When employed as a wound covering material, the water permeability of the membrance will be selected to avoid both water accumulation beneath the covering and desiccation of the wound. It is contemplated that a series of coverings having gradated permeabilities will be prepared.

The present invention employs a physiologically acceptable polyurethane substrate or membrane which is graft polymerized with hydrophilic monomer(s), as will be described below. The polyurethahe substrate will be in the form of a film or sheet having a thickness which is suitable for application over a wound. The thickness will usually be in the range from about 5 to 100 microns, more usually in the range from about 10 to 60 microns, although a thickness outside of these ranges may be useful under certain circumstances. The remaining dimensions of the polyurethane membrane are not critical, although the membrane will usually be cut into sheets which are suitably sized for processing.

Polyurethanes suitable for use in the present invention include polyester polyurethanes. The polyesters are formed by condensation of a polycarboxylic acid ester with a diol or OH-capped lactone, and thereafter reacted with a suitable diisocyanate to form an alternating or block copolymer having a preselected ratio of polyester to diisocyanate. Desirably, the diisocyanate will include activated methylenes which can serve as initiation sites. Particularly, methylenes may be activated by aryl groups, e.g. phenyl.

The polyurethane substrate will usually be cross-linked, and the degree of cross-linking and ratio of polyester to diisocyanate will be selected to provide a modulus of elasticity having an upper limit of about 2000 PSI, usually about 1500 PSI, preferably about 750 PSI. The lower limit will be about 100 PSI, usually about 250 PSI. The polyurethane should also have an elongation at break of at least about 500% with no upper limit, usually being in the range from about 500% to 2000%.

Preferred polyester polyurethanes are characterized by a recurring unit having the following formula:

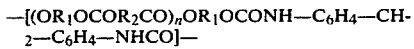

where $R_1$ and $R_2$ may be the same or different and are a group $—(CH_2)_x—$ where x is an integer from 1 to 8, usually frdm 2 to 6, more usually 4, and where n is the ratio of the polyester to diisocyanate having an average value in the range from about 2.5 to 50, more usually in the range from 2.5 to to 20, preferably from about 3.5 to 8.

Polyurethanes having the above formula may be prepared by copolymerization of butanediol, adipic acid and p,p'-diphenylmethane diisocyanate, where the butanediol and adipic acid are first reacted to form the polyester diol, which diol is subsequently reacted with the diisocyanate to form the polyurethane polymer. Suitable polyurethanes are commercially available under the tradename Platilon U02 from Plate Bonn, West Germany and Plamex from Beith-Shemesh, Israel.

The hydrophilic monomers will be capable of graft polymerization with the polyurethane substrate just described. The monomer will be highly soluble in water, including nonbound —OH, —COOH, —NH$_2$, —NH, which are soluble in water, usually at least about 1 g/L. The monomer should also be relatively small, usually below about 300 daltons, more usually below about 200 daltons, allowing penetration of the monomer into the substrate during graft polymerization.

In particular, suitable hydrophilic monomers include vinyl monomers, e.g., acrylamides, such as acrylamide, N-methylol acrylamide, N-ethylol acrylamide; acrylates, such as acrylic acid, hydroxyethyl acrylate, hydroxypropyl acrylate, 2,3-dihydroxypropyl acrylate, 2,3-epoxypropyl acrylate; methacrylates, such as methacrylic acid, hydroxyethyl methacrylate, hydroxypropyl methacrylate, 2,3-dihydroxypropyl methacrylate, 2,3-epoxypropyl methacrylate; and the like. Also useful is N-vinyl pyrrolidone. Such hydrophilic monomers may be introduced singly or in combination. Particularly preferred is the use of an acrylamide monomers.

The hydrophilic monomers are reacted with the polyurethane substrate by graft polymerization to form the hydrophilic copolymer of the present invention. General methods for graft polymerization are taught by Chapiro, supra. In particular, the polyurethane substrate may be immersed in an aqueous solution containing a preselected concentration of the monomer (usually about 5 to 50% by weight) and a homopolymerization inhibitor, typically a transition metal salt. Graft polymerization may be initiated by conditions which produce reactive radicals on the polymer. Conveniently, x-ray or gamma radiation, or an initiator such as a cerium (Ce$^{+4}$) salt are suitable. When radiation is used for initiation, a total dose of about 100–700 krad applied over a 0.5 to 5 hour period will be sufficient, depending on the dose rate. If chemical initiation is used, a cerium salt concentration of about 20 mM and reaction time of from 10–20 hours are adequate. The reaction is usually carried out at ambient temperature and pressure.

Suitable homopolymerization inhibitors include transition metal salts, such as cerium, cupric, ferric, ferrous and vanadium salts. Preferred are cerium (Ce$^{+4}$) salts, particularly ceric ammonium nitrate (Ce(NH$_4$)$_2$(NO$_3$)$_6$). Ce$^{+4}$ salts may serve both as graft polymerization initiators and homopolymerization inhibitors.

The water permeability of the wound covering material of the present invention will depend primarily on the thickness of the polyurethane substrate and on the nature of the hydrophilic monomer introduced. By increasing the thickness of the substrate membrane, the water permeability of the resulting hydrophilic membrance will be reduced. Also, it has been found that choice of the monomer will affect the permeability of the product. Acrylamide provides relatively high water permeability (from 5000 to 8000 g/m$^2$/24) as a percent graft ranging from 21% to 146%, while hydroxyethyl methacrylate provides a much lower permeability (2400 to 3000 g/m$^2$/24 hour) at comprable grafting percentages (70% to 117%). Thus, a material having a preselected permeability may be produced by properly choosing the thickness of the substrate and identity of the monomer(s).

The amount of hydrophilic monomer introduced will be at least about 40%, preferably at least about 50%. Wound covering material having less than 50% graft monomer, while displaying adequate permeability, will be less elastic than materials having above 50% monomer. Thus, it is preferred that the materials have greater than 50% monomer. Materials having less than about 40% monomer are insufficiently elastic to serve as wound coverings. The maximum amount of monomer which may be introduced is less critical. The upper limit will be about 400%, more usually about 175%.

All weight percentages are determined by weighing the polyurethane substrate before and after grafting, and calculating the percentage as $100 \times (w_g - w_i)/w_i$ where $w_i$ and $w_g$ represent the weight of the initial and grafted substrate, respectively. In determining the weight percentages reported hereinafter, the polyurethane substrate was washed and dried thoroughly at 50° C. under vacuum before weighing.

The modulus of elasticity of the hydrophilic membrane of the present invention will be below about 600 PSI, preferably below about 350 PSI. Such high elasticity is a considerable advantage when the membrane is used as a wound covering since it allows the material to conform to the wound and to stretch as necessary as the patient moves. The lower limit of elasticity is less critical, usually being above about 100 PSI, more usually above 150 PSI.

Exemplary formulations and methods of preparation for the product of the present invention are set forth in the Experimental section, hereinafter. Particularly suitable is the product of Example 1.

The wound covering material produced by the method of the present invention will be slightly thicker (5%–40%) than the substrate material. The area of the product, however, will usually increase from about 50% to 150% relative to the substrate. The product is dimensionally stable and insensitive to variations in water absorbency. This is an advantage since the covering will not shrink as the wound heals and the water flux from the wound decreases. Such shrinkage would cause severe discomfort in the patient.

The hydrophilic membrane of the present invention is relatively inelastic when dry, but highly elastic after absorbing water. The modulus of elasticity of the product hydrophilic membrane (when hydrated or wet) will be below 600 PSI, as described above. In constrast, the dry hydrophilic membrane will have a modulus of elasticity above 2000 PSI, more usually above 2500 PSI. Water absorbance takes place after several seconds when applying the membrane to a wet surface (such as an open wound) or immersing it in water. The dry material is non-adherent and may be stored without a backing film. The surface of the material, however, is hydrophilic and will adhere to moist locations, e.g., wounds which are to be covered.

Typically, the wound covering material will be dried, sterilized and stored in a sealed packing to maintain its sterile condition. Sterilization may be achieved using a gaseous sterilant; e.g., ethylene oxide, radiation, or other conventional techniques.

The hydrophilic mombrane will be used primarily as a wound covering material, especially for major trauma resulting in total or partial destruction of the epidermal layer. Such wounds cause elevated loss of water, requiring the enhanced water permeability of the present invention. Moreover, the increase water flux from the wound will keep the wound covering hydrated. Wounds suitable for treatment are typically caused by burns (second and third degree), severe abrasions, ulcers, and donor sites for use in skin grafting. The wound coverings of the present invention will find use both on humans and on other animals requiring treatment.

In use, the wound covering material will usually be applied dry to the wound, although the material may be wetted in a physiologically acceptable medium, e.g., saline. When applied dry, moisture from the wound will be immediately absorbed, causing the covering material to become pliable. The covering material will conform and adhere to the surface of the wound until the wound heals or the covering is removed for further treatment. As the wound heals, the water flux is reduced, causing the wound covering material to dry and allowing its easy removal from the skin. Although the covering material need not be secured to the skin, it may sometimes be desirable (particularly in veterinary use where the animals may attempt to dislodge the covering) to provide means for securing the covering along the edges to the adjacent intact skin. Conveniently, the coverings may be secured by sutures, tape, or adhesives such as cyano acrylate.

The hydrophilic membrane of the present invention may be combined with effective amounts of anesthetics, antibiotics, and antiseptics, and other drugs, typically present at about 0.001 to 2% by weight. The drug(s) may be applied to the membrane in an aqueous base, and the membrane stored in a wet or dried condition, depending on the nature of the drug. Many drugs may be applied directly to the surface of the wound covering and transported to the surface of the wound, thus eliminating the need to remove the wound covering.

EXPERIMENTAL

The following examples are offered by way of illustration, not by way of limitation. The following abbreviations are used:
RH—relative humidity
AAm—acrylamide
HEA—hydroxyethyl acrylate
HEMA—hydroxyethyl methacrylate
AA—acrylic acid Water flux, as used in the specification and claims and measured in the Experimental section, was measured at 37° C. and 60% RH according to ASTM E96-66 (Inverted Water Method). All percentages are by weight unless other wise indicated.

Preparation of Graft Polymers

EXAMPLE 1

A sheet of polyester polyurethane (30μ thick) having a recurring unit of the formula:

with average n=6.5 and having a modulus of elasticity of 525 PSI and elongation at break of 950% (Platilon U02), was immersed in a test tube containing freshly prepared 20% AAm in 20 mM aqueous $Ce(NH_4)_2(NO_3)_6$ solution. The $Ce^{4+}$ salt is a homopolymerization inhibitor for the AAm. The test tube and its contents were irradiated at room temperature in the presence of air with a $^{60}Co$ gamma source for 120 min. receiving a total dose of 240 krad. The sheet was removed from the test tube and washed with warm water for several hours, then dried in a vacuum oven at 50° C. to a constant weight. A graft of 115% (by weight as defined above) was obtained. The water permeability of the grafted membrane was measured and found to be 6800 g/m²/24 hr. The amount of water absorbed by the film was about 110% of the total film weight. Elasticity was determined to be acceptable by qualitative observation.

EXAMPLE 2

Example 1 was repeated except that the dose rate was decreased so that the total dose absorbed by the sample was 150 krad, producing a membrane having a 106% graft. The water permeability was 7600 g/m$^2$/24 hr., and the water absorbed by the membrane was about 100% of the total film weight. Elasticity was acceptable.

EXAMPLE 3

Example 1 was repeated except that the Ce(NH$_4$)$_2$(NO$_3$)$_4$ concentration was increased to 40 mM, producing a membrane having a 146% graft. The water permeability of the membrane was 7000 g/m$^2$/24 hr, and the water absorption was about 150% of the total film weight. Elasticity was acceptable.

EXAMPLE 4

Example 1 was repeated except that the Ce(NH$_4$)$_2$(NO$_3$)$_6$ concentration was increased to 50 mM and the irradiation time was increased to 180 min. The total dose absorbed by the sample was 360 krad, producing a membrane having a 163% graft. The water permeability was 7600 g/m$^2$/24 hr, and the water absorption was about 150% of the total film weight. Elasticity was acceptable.

EXAMPLE 5

Example 1 was repeated except that the irradiation dose rate was decreased to 1.3 krad/min. and irradiation time was 100 min. The resulting membrane contained 82% graft. The water permeability of the membrane was 7200 g/m$^2$/24 hr, and the water absorption was about 90% of the total film weight. Elasticity was acceptable.

EXAMPLE 6

Example 4 was repeated except that the Ce(NH$_4$)$_2$(NO$_3$)$_6$ was replaced by 40 mM Ce(SO$_4$)$_2$ made 0.2 N in H$_2$SO$_4$. The resulting membrane contained 42% graft. The water permeability of the membrane so produced was 6900 g/m$^2$/24 hr, and the water absorption about 50% of the total film weight. The elasticity of the prepared membrane was perceptably less than the membranes of Examples 1–5, and the membrane was considered to have only marginally sufficient elasticity to serve as a wound covering.

EXAMPLE 7

Example 4 was repeated except that the Ce(NH$_4$)$_2$(NO$_3$)$_6$ was replaced by 40 mM Ce(NH$_4$)$_2$(SO$_4$)$_3$. The resulting membrane contained 57% graft. The water permeability of the membrane was 5800 g/m$^2$/24 hr, and the water absorption about 60% of the total film weight. Elasticity was acceptable.

EXAMPLE 8

Example 7 was repeated except that the Ce(NH$_4$)$_2$(SO$_4$)$_3$ was increased to 100 mM. The resulting membrane contained 59% graft. The water permeability of the membrance was 7000 g/m$^2$/24 hr, and the water absorption about 60% of the total film weight. Elasticity was acceptable.

EXAMPLE 9

Example 8 was repeated except that the irradiation time was doubled to 360 min. The total dose absorbed by the sample was 720 krad, producing a membrane having a 64% graft. The water permeability of the membrane was 6400 g/m$^2$/24 hr, and the water absorption was about 60% of the total film weight. Elasticity was acceptable.

EXAMPLE 10

Example 4 was repeated except that the Ce(NH$_4$)$_2$(NO$_3$)$_6$ was replaced by 20 mM Cu(NO$_3$)$_2$. The resulting membrance contained 63% graft. The water permeability of the membrane so produced was 7200 g/m$^2$/24 hr, and the water absorption was about 50% of the total film weight. Elasticity was acceptable.

EXAMPLE 11

Example 10 was repeated except that the Cu(NO$_3$)$_2$ was replaced by 100 mM CuSO$_4$. The resulting membrane contained 43% graft. The water permeability of the membrane was 7200 g/m$^2$/24 hr. Elasticity was only marginally acceptable.

EXAMPLE 12

Example 4 was repeated except that the Ce(NH$_4$)$_2$(NO$_3$)$_6$ was replaced by 20 mM of FeSO$_4$ and the dose rate cut into half so that the total dose absorbed by the sample was 180 krad. The resulted membrane had 41% graft. The water permeability of the membrane so produced was 7900 g/m$^2$/24 hr and the water absorbance was about 30% of the total film weight. Elasticity was only marginally acceptable.

EXAMPLE 13

Example 11 was repeated except that the CuSO$_4$ was replaced by 20 mM Fe$_2$(SO$_4$)$_3$ and the solution made 0.2 N in H$_2$SO$_4$. The resulting membrane contained 21% graft. The water permeability of the membrane so produced was 7200 g/m$^2$/24 hr and the water absorbance was about 20% of the total film weight. This product was not sufficiently elastic to be acceptable as a wound covering material.

EXAMPLE 14

Example 13 was repeated except that the concentration of Fe$_2$(SO$_4$)$_3$ was increased to 50 mM and the acidity made 0.5 N in H$_2$SO$_4$. The resulting membrane contained 22% graft. The water permeability of the membrane so produced was 5700 g/m$^2$/24 hr and the water absorbance was about 20% of the total film weight. Elasticity was unacceptable.

EXAMPLE 15

Example 14 was repeated except that the Fe$_2$(SO$_4$)$_3$ was replaced by 50 mM Ti$_2$(SO$_4$)$_3$ and the solution made 1 N in H$_2$SO$_4$. The resulting membrane contained 26% graft. The water permeability of the membrane so produced was 6200 g/m$^2$/24 hr and the water absorbance was about 30% of the total film weight. Elasticity was unacceptable.

EXAMPLE 16

Example 15 was repeated except that the Ti$_2$(SO$_4$)$_3$ was replaced by 20 mM Ti(SO$_4$)$_2$ and the acidity decreased to 0.3 N in H$_2$SO$_4$. The resulting membrane contained 37% graft. The water permeability of the membrane so produced was 6200 g/m$^2$/24 hr and the water absorbance was about 40% of the total film weight. Elasticity was unacceptable.

EXAMPLE 17

Example 4 was repeated except that the $Ce^{4+}$ salt was replaced by 20 mM of $VOCl_2$. The resulting membrane contained 86% graft. The water permeability of the membrane was 6700 $g/m^2/24$ hr and the water absorbance was about 80% of the total film weight. Elasticity was acceptable.

EXAMPLE 18

Example 17 was repeated except that the $VOCl_2$ was replaced by 20 mM of $VCl_3$. The resulting membrane contained 77% graft. The water permeability of the membrane was 7600 $g/m^2/24$ hr and the water absorbance was about 90% of the total film weight. Elasticity was acceptable.

EXAMPLE 19

Example 10 was repeated except that the 20% AAm was replaced by 20% HEMA and the $Cu(NO_3)_2$ concentration was increased to 200 mM. The resulting membrane contained a graft of 70%. The water permeability was 2400 $g/m^2/24$ hr and the water absorbance was about 40% of the total film weight. Elasticity was marginal.

EXAMPLE 20

Example 19 was repeated except that the solution was bubbled with $N_2$ for 30 min. prior to irradiation and kept under nitrogen atmosphere during irradiation. The resulting membrane contained a graft of 117%. The water permeability was 3000 $g/m^2/24$ hr and the water absorbance was about 30% of the total film weight. Elasticity was marginal.

EXAMPLE 21

Example 19 was repeated except that the HEMA was replaced by 20% HEA and the $Cu(NO_3)_2$ decreased to 20 mM. The resulting membrane contained a graft of 64%. Elasticity was margin.

EXAMPLE 22

Example 20 was repeated except that the HEMA was replaced by 10% AA. The $Cu(NO_3)_2$ concentration was decreased to 20 mM, and the irradiation dose increased to 540 krad. The resulting membrane contained 32% graft. The acid form of the grafted sheet was not easy to handle when dry because of self-adherence. In immersing the membrane into diluted $Na_2CO_3$ solution the acid groups were neutralized and the self-adherence disappeared. Elasticity was unacceptable.

EXAMPLE 23

Example 1 was repeated except that the polyurethane was obtrained from a different batch where the ratio between the polyester and the diisocyanate in the polyurethane was 3.8 (n in the formula given in Example 1), the modulus of elasticity was 510 PSI, and elongation at break was 910%. The resulting membrane contained a graft of 62%. The water permeability was 7300 $g/m^2/24$ hr and the water absorbance was about 80% of the total film weight. Elasticity was acceptable.

EXAMPLE 24

Example 1 was repeated except that the polyurethane was Plamex where the ratio between the polyester and the diisocyanate in the polyurethane (n) was 2.6, the modulus of elasticity was 960 PSI, and the elongation at break was 580%. The irradiation time was increased to 150 min. so that the total dose absorbed by the sample was 300 krad. The resulting membrane contained a graft of 44%. The water permeability was 5600 $g/m^2/24$ hr and the water absorbance was about 30% of the total film weight. Elasticity was marginal.

EXAMPLE 25

Example 24 was repeated except that the polyurethane used was Tuftane®, B. F. Goodrich, Akron, Ohio having a modulus of elasticity of 2360 PSI and elongation at break of 360% (n =2.7 in the formula of Example 1). The resulting membrane contained a graft of 18%. The membrane thus produced had a hydrophobic surface, insufficient elasticity and was not suitable for use as an artificial skin.

The results of Experiments 1–25 are summarized in Table 1.

TABLE 1

| Exp. # | Starting Material | Monomer | Inhibitor | Radiation | Graft | Permeability ($g/m^2/24$ hr) | Absorbency | Elasticity |
|---|---|---|---|---|---|---|---|---|
| 1 | n = 6.5 | 20% AAm | 20 mM $Ce(NH_4)_2(NO_2)_6$ | 240 krad | 115% | 6800 | 110% | acceptable |
| 2 | " | " | 20 mM $Ce(NH_4)_2(NO_2)_6$ | 150 krad | 106% | 7600 | 100% | " |
| 3 | " | " | 40 mM $Ce(NH_4)_2(NO_2)_6$ | 240 krad | 146% | 7000 | 150% | " |
| 4 | " | " | 50 mM $Ce(NH_4)_2(NO_2)_6$ | 360 krad | 163% | 7600 | 150% | " |
| 5 | " | " | 20 mM $Ce(NH_4)_2(NO_2)_6$ | 130 krad | 82% | 7200 | 90% | " |
| 6 | " | " | 40 mM $Ce(SO_4)_2$ 0.2 N $H_2SO_4$ | 240 krad | 42% | 6900 | 50% | marginal |
| 7 | " | " | 40 mM $Ce(NH_4)_2(SO_4)_3$ | 240 krad | 57% | 5800 | 60% | acceptable |
| 8 | " | " | 100 mM $Ce(NH_4)_2(SO_4)_3$ | 240 krad | 59% | 7000 | 60% | " |
| 9 | " | " | 100 mM $Ce(NH_4)_2(SO_4)_3$ | 720 krad | 64% | 6400 | 60% | " |
| 10 | " | " | 20 mM $Cu(NO_3)$ | 360 krad | 63% | 7200 | 50% | " |
| 11 | " | " | 100 mM $CuSO_4$ | 260 krad | 43% | 7200 | * | marginal |
| 12 | " | " | 20 mM $FeSO_4$ | 180 krad | 41% | 7900 | 30% | " |
| 13 | " | " | 20 mM $Fe_2(SO_4)_3$ 0.2 N $H_2SO_4$ | 360 krad | 21% | 7200 | 20% | unacceptable |
| 14 | " | " | 50 mM $FeSO_4$ 0.5 N $H_2SO_4$ | 360 krad | 22% | 5700 | 20% | " |
| 15 | " | " | 50 mM $Ti_2(SO_4)_3$ 1 N $H_2SO_4$ | 360 krad | 26% | 6200 | 30% | " |
| 16 | " | " | 20 mM $Ti(SO_4)_2$ 0.3 M $H_2SO_4$ | 360 krad | 37% | 6200 | 40% | " |
| 17 | " | " | 20 mM $VOCl_2$ | 360 krad | 86% | 6700 | 80% | acceptable |
| 18 | " | " | 20 mM $VCl_3$ | 360 krad | 77% | 7600 | ~90% | " |
| 19 | " | HEMA 20% | 200 mM $Cu(NO_3)_2$ | 360 krad | 70% | 2400 | 40% | marginal |
| 20 | " | HEMA 20% | 200 MM $Cu(NO_3)_2$ | 360 krad | 117% | 3000 | 30% | " |

TABLE 1-continued

| Exp. # | Starting Material | Monomer | Inhibitor | Radiation | Graft | Permeability (g/m²/24 hr) | Absorbency | Elasticity |
|---|---|---|---|---|---|---|---|---|
| 21 | " | HEA | 20 mM CuNO₃ | 360 krad | 64% | * | * | marginal |
| 22 | " | AA 10% | 20 mM CuNO₃ | 540 krad | 32% | * | * | unacceptable |
| 23 | n = 3.8<br>510 modulus<br>910% elongation | 20% AAm | 20 mM Ce(NH₄)₂(NO₂)₆ | 240 krad | 62% | 7300 | 80% | acceptable |
| 24 | n = 2.6<br>960 modulus<br>580% elongation | 20% AAm | 20 mM Ce(NH₄)₂(NO₂)₆ | 300 krad | 44% | 5600 | 30% | marginal |
| 25 | n = 2.7<br>960 modulus | 20% AAm | 20 mM Ce(NH₄)₂(NO₂)₆ | 300 krad | 18% | hydrophobic | * | unacceptable |

*not determined

EXAMPLES 26-30

Sheet samples of polyester polyurethane (30μ thick) as in Example 1 were immersed in aqueous solution containing 20% AAm and 20 mM Ce(NH₄)₂(NO₃)₆ at 21±2° C. for different periods of time. The sheets were removed from the solution and washed thoroughly with warm water for several hours and the amount of graft was determined. The results of these experiments are given in Table 2.

TABLE 2

Percent of graft on polyurethane in 20% AAm aqueous solution contained 20 mM Ce(NH₄)₂(NO₃)₆ at 21° C., without gamma irradiation.

| Example No. | Reaction time, hours | % Graft |
|---|---|---|
| 26 | 6 | 15 |
| 27 | 10 | 37 |
| 28 | 12 | 45 |
| 29 | 14 | 87 |
| 30 | 20 | 385 |

Changes in tensile properties of polyurethane films grafted with different percentages of AAm in dry and wet states were measured under controlled RH conditions and are given in Table 3.

TABLE 3

Tensile properties of AAm grafted polyurethane membranes as a function of percent of graft, in the dry and wet states, measured at a strain rate of 2 cm/min. and 25° C.

| Percent graft | Elongation at break (%) | | Tensile Strength at break (PSI) | | Modulus at 100% Elongation (PSI) | |
|---|---|---|---|---|---|---|
| | dry* | wet** | dry* | wet** | dry* | wet** |
| 55 | 385 | 1070 | 5830 | 1830 | 2790 | 180 |
| 62 | 330 | 950 | 6140 | 1730 | 3020 | 210 |
| 73 | 325 | 880 | 6180 | 1950 | 3170 | 220 |
| 88 | 295 | 630 | 6245 | 2290 | 3420 | 280 |

*Measured at 50% RH
**Soaked in water and measured at 96% RH

Clinical Results

Polyacrylamide-grafted polyurethane membranes with add-on ranging from 60 to 160% were used on 20 patients in various clinical situations, such as burns, donor sites and ulcers. The membranes were prepared as described in Examples 1, 2, 3, 5, 7, 10, 19 and 23.

The membranes were applied either in the wet or dry state. In the former case the membrane was immersed in saline solution for a few seconds before use. The membrane changes its appearance and became slightly opaque and pliable when wet but still transparent enough to observe any undergoing process underneath the cover. Upon application there was immediate adherence of the membrane to the denuded area without the need for suturing, as is usually practiced in skin grafting. The membranes remained attached until they were removed, or until a complete healing occurred underneath them. Then they were peeled off by mere washing with water. Any area where the epidermis reached complete recovery the membrane peeled off by itself. Other areas, like ulcers, demonstrated a good granulation tissue underneath it, and in due time, the membrane was peeled off by the treating surgeon and the area was recovered by skin graft.

One of the striking observations was the cessation of pain. Out of 20 patients, in 18 cases very good results were obtained, i.e., healing of epidermis under the membrane, or healing of donor area, or preparing the bed for final skin grafting. The membranes are convenient, pliable and self-adherent. There was no sensitivity to them and no infection. In 3 patients, there were hematoma underneath the cover that needed evacuation, but did not interfere with the healing process itself. The membranes remained attached to the treated areas between 3 to 21 days. Most of the wound sizes treated were around 200 cm².

The material of the present invention was tested to assess delayed contact hypersensitivity and dermal irritation. The material was prepared as described in Experiment 1, except that varying radiation doeses were employed to provide graft polymers having the following characteristics:

| Batch No. | Graft | Permeability | Elasticity | Absorbancy |
|---|---|---|---|---|
| 1 | 113% | 5810 g/m²/24 hr. | * | 93% |
| 2 | 103% | 5050 g/m²/24 hr. | 174 PSI | 88% |
| 3 | 129% | 5560 g/m²/24 hr. | 216 PSI | 94% |
| 4 | 97% | 5940 g/m²/24 hr. | * | 78% |
| 5 | 67% | * | * | * |
| 6 | 50% | * | * | * |

* - not measured

1. Delayed Hypersensitivty Tests

Young male and female guinea-pigs of outbred Hartley strain were used. The supplier was A. Loebenstein Laboratory Animals (Yokneam, Israel). The albino guinea-pig is the standard model for this type of study. Animals were within the weight range of 200-350 g. The test group consisted of ten male and ten female animals and the control group of five male and five female animals. The control animals did not participate in the induction phase but were treated identically to the test group at challenge. The animals were treated with test material from each of the batches.

An area of skin (5×5 cm) on the left dorso-lateral line of the test group animals was clipped free of hair on the day before treatment started and on Days 7, 14 and 28. A similar area on the right dorso-lateral line of all animals was shaven on Day 28. Chemical depilatories were not used. On Days 1, 8 and 15 the shaven skin of each test group animal was abraded by drawing the blunt edge of a scalpel tip across the skin, making a lattice pattern of parallel abrasions at intervals of 5-10 mm. The abrasions were intended to break the stratum corneum of the epidermis without damaging the underlying tissues or causing bleeding. This abrasion procedure was designed to mimic the intended human exposure to the test material. A rectangular piece of the test material approximately 3×3 cm was placed on the shaved abraded skin and this was then covered with an air-tight occlusive dressing which remained in place for six hours. After the six-hour exposure period, the bandages and the test material were removed. On the morning after exposure each animal was examined and any skin responses were recorded.

Control and test groups of animals were treated identically at challenge on Day 29. A 3×3 cm square of the test material (chosen randomly from the prepared batches) was applied to the abraded right dermal test site and covered by an occlusive bandage. After a six-hour exposure period the bandages and the test material were removed.

Skin reactions to challenge were assessed 24 and 48 hours after application of the challenge dose. Three hours before the first assessment, the dermal test sites were depilated with suitable cream (Depilan Hamol International, Switzerland) and washed with warm water. Erythema and indurate swelling of the challenged dermal test sites constituted visible signs of a delayed contact hypersensitivity reaction.

None of the animals exhibited any skin responses following test material application. None of the animals of either the test or control group exhibited any skin reaction to test material application. All animals made expected bodyweight gains during the study period. Under the conditions of this test, no evidence was found that material of the present invention could cause delayed hypersensitivity reactions.

2. Irritation Tests

A local strain of remote New Zealand White albino rabbits from A. Loebenstein Laboratory Animals, Yoqneam, Israel, was used. The treatment group consisted of six young adult rabbits. Rabbits numbers 929M, 942M and 948M were treated with test material from batches 2 and 4 while rabbits numbers 930M, 932M and 938M were treated with test material from batches 2 and 3.

The rabbit was securely restrained by a technician. The left side of the shaved dorsum was abraded by drawing the tip of a lancet across the skin forming a lattice pattern with parallel abrasions at Intervals of 5-10 mm. The abrasions were such as to break the stratum corneum of the epidermis without damaging the underlying tissues or cause bleeding. The right side of the shaved dorsum was left intact. The use of an abraded test site is in consideration of the intended human use of the test material.

Squares of the test material measuring approximately 2.5 cm were applied one to each of the abraded and intact treatment sites. Both patches were covered by slightly larger sheets of impervious non-reactive material and were kept in place by a non-irritant dressing and an adhesive bandage which was wrapped around the trunk of the rabbit with sufficient tension to ensure that the test material was in close contact with the skin.

After the occlusive dressings were secured, the animals were returned to their cages. Regular checks were made while the dressing was in place to ensure that the animals were not in distress or developing clinical signs of reaction to treatment. The dressings were removed at the end of the 24-hour exposure period. Assessment of skin irritation responses were not made until any transient irritation responses provoked by stripping off the bandages had subsided. Skin irritation responses of the intact and abraded test sites were assessed 30 to 60 minutes, 24, 48 and 72 hours after patch removal. Reactions at the test sites were assessed according to the criteria of Draize, J. H. Dermal Toxicity. In: "Appraisal of the Safety of Chemicals in Food, Drugs and Cosmetics". Association of Food and Drug Officials of the United States, Austin, Tex., pp. 46-49 (1959).

No signs of dermal irritation were seen at any of the examinations. Under the conditions of this study the material of the present invention was assessed as being non-irritant to the skin.

According to the present invention, a synthetic wound covering material is provided which permits a controlled flux of water from the wound, thus preventing both fluid accumulation beneath the covering and desiccation of the wound. The wound covering may be easily removed at any time by immersion in water. Also, as the wound heals, the wound covering will dry and peel from the healed skin.

Although the foregoing invention has been described in some detail for purposes of clarity of understanding, it will be appreciated by those skilled in the art that certain modifications and variations may be practiced without departing from the scope of the invention as expressed in the following claims.

What is claimed is:

1. A synthetic wound covering comprising a hydrophilic membrane which is a graft polymer formed from a polyester polyurethane substrate having a modulus of elasticity below 1500 PSI and a hydrophilic acrylamide monomer wherein the monomer is present at at least 50% by weight and is substantially uniformly dispersed through the substrate, whereby the graft polymer has a water permeability in the range from 1000 to 8000 g/m$^2$/24 hr and a modulus of elasticity below about 600 PSI when wet.

2. A synthetic wound covering according to claim 1, having a thickness in the range from 10 to 100 microns.

3. A synthetic wound covering according to claim 1, wherein the polyurethane is a polyester polyurethane having a recurring unit of the formula

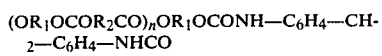

in which $R_1$ and $R_2$ may be the same or different and are each a group —$(CH_2)_x$— where x is an integer of 1 to 8 and n has an average value of 2.5 to 20.

4. A synthetic wound covering according to claim 3, wherein average n is from 2.5 to 8.

5. A synthetic wound covering according to claim 3, wherein $R_1$ and $R_2$ are each a tetramethylene group —$(CH_2)_4$—.

6. A wound covering material comprising a graft polymer formed from a polyester polyurethane substrate having a modulus of elasticity below 1500 PSI and a hydrophilic acrylamide monomer present at at least 50% by weight, said material having a water permeability in the range from 1,000 to 8,000 g/m$^2$/24 hr and a modulus of elasticity below 600 PSI when wet, wherein said covering is sterilized and enclosed in a sealed package.

7. A wound covering material as in claim 6, having a drug uniformly dispersed at about from 0.001 to 2 weight percent.

8. A method for treating a wound, said method employing a wound covering material comprising a graft polymer formed from a polyester polyurethane substrate having a modulus of elasticity below about 1500 PSI and a hydrophilic acrylamide monomer present at at least 50% by weight, said material having a water permeability in the range from 1000 to 8,000 g/m$^2$/24 hr and modulus of elasticity below 600 PSI when wet, said method comprising:
applying the covering material to the wound such that the covering conforms to the surface of the wound.

9. A method as in claim 8, wherein the covering is dry when applied to the wound.

10. A method as in claim 8 wherein the covering is wetted prior to applying to the wound.

11. A method as in claim 8, wherein the covering material is secured to the wound by external means.

12. A process for preparing an elastic hydrophilic membrane, said process comprising graft polymerizing a hydrophilic acrylamide monomer onto a Polyeater polyurethane substrate, wherein said substrate has a modulus of elasticity in the range from 150 to 1500 PSI and the polymerization is continued for an amount of time sufficient to yield a product having at least 50 weight percent hydrophilic acrylamide monomer and a water permeability in the range from 1,000 to 8,000 g/m$^2$/24 hr.

13. A process as in claim 12, wherein graft polymerization is initiated by radiation.

14. A process as in claim 12, wherein graft polymerization is chemically initiated by a cerium salt.

15. A process for preparing an elastic hydrophilic membrane, said process comprising:
preparing a reaction medium having preselected concentrations of a hydrophilic acrylamide monomer and a homopolymerization inhibitor;
immersing a polyester polyurethane substrate in the reaction medium, said substrate having a modulus of elasticity in the range from 150 to 1500 PSI; and
initiating graft polymerization between the monomer and the substrate and continuing such polymerization for a time sufficient to cause a weight increase of at least 50% relative to the initial weight of the substrate and the resulting hydrophilic membrane attains a water permeability in the range from 1,000 to 8,000 g/m$^2$/24 hr.

16. A process as in claim 15, wherein the polyester polyurethane substrate has an elongation at break of at least 500%.

17. A process as in claim 15, wherein the polyester polyurethane has a recurring unit of the formula:

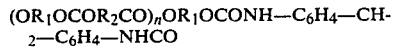

in which $R_1$ and $R_2$ may be the same or different and are each a group —$(CH_2)_x$— where x is an integer of 1 to 8 and n has an average value of 2.5 to 20.

18. A process as in claim 15, wherein the homopolymerization inhibitor is a transition metal salt.

19. A process as in claim 18, wherein the transition metal salt is cerium salt.

20. A process as in claim 18, wherein the transition metal salt a ceric ammonium nitrate.

21. A hydrophilic membrane produced in accordance with the method of claim 15.

* * * * *